United States Patent
Ardehali et al.

[11] Patent Number: 6,126,955
[45] Date of Patent: Oct. 3, 2000

[54] APO-TRANSFERRIN AS A POTENT INHIBITOR OF BACTERIAL ADHESION TO BIOMATERIALS

[75] Inventors: Reza Ardehali; Jarmila Janatova; S. Fazal Mohammad; Gregory L. Burns, all of Salt Lake City, Utah

[73] Assignee: University of Utah Research Foundation, Salt Lake City, Utah

[21] Appl. No.: 09/293,823

[22] Filed: Apr. 16, 1999

Related U.S. Application Data

[60] Provisional application No. 60/082,177, Apr. 16, 1998.
[51] Int. Cl.[7] .............................. A61F 13/00; A61K 9/14; A61K 9/16
[52] U.S. Cl. ........................... 424/422; 424/489; 424/491
[58] Field of Search .................................... 424/489, 491, 424/422; 514/411

[56] References Cited

U.S. PATENT DOCUMENTS 5,753,506  5/1998  Johe ......................................... 435/377
5,811,447  9/1998  Kunz et al. .............................. 514/411

OTHER PUBLICATIONS

Grange et al., Transferrin associated with the porcine intestinal mucosa is a receptor specific for K88ab fimbriae of *Escherichia coli*, Infect Immun, 0019–9567, Abstract, Feb. 1996.
Modun et al., The *Staphylococcus Aureus* and *Staphylococcus epidermidis* transfferin–binding protiens are expressed in vivo during infection, Microbiology, 1350–0872, Abstract, Apr. 1998.

P.E. Vaudaux et al., Use of Adhesion–Defective Mutants of *Staphylococcus aureus* To Define the Role of Specific Plasma Proteins in Promoting Bacterial Adhesion to Canine Arteriovenous Shunts, 63 Infection and Immunity 585–590 (1995).
W.M. Artis et al., Fungistatic Mechanism of Human Transferrin for *Rhizopus oryzae* and *Trichophyton mentagrophytes*: Alternative to Simple Iron Deprivation, 41 Infection and Immunity 1269–1278 (1983).
R.T. Ellison III et al., Lactoferrin and transferrin damage of the Gram–negative outer membrane is modulated by $Ca^{2+}$ and $Mg^{2+}$, 136 Journal of General Microbiology 1437–1446 (1990).
R.T. Ellison III et al., Damage of the Outer Membrane of Enteric Gram–Negative Bacteria by Lactoferrin and Transferrin, 56 Infection and Immunity 2774–2781 (1988).
P. Williams & E. Griffiths, Bacterial transferrin receptors—structure, function and contribution to virulence, 181 Medical Microbiology and Immunology 301–322 (1992).
D.E. Benson et al., Effects of Plasma on Adhesion of Biofilm Forming *Pseudomonas aeruginosa* an *Staphylococcus epidermidis* to Fibrin Substrate, 42 ASAIO Journal M655–M660 (1996).

*Primary Examiner*—Thurman K. Page
*Assistant Examiner*—Susan Tran
*Attorney, Agent, or Firm*—Clayton, Howarth & Cannon, P.C.

[57] ABSTRACT

Methods of inhibiting bacterial adhesion to medical implants and reducing device-associated infection are effectuated by administering an effective amount of apo-transferrin to an individual with such an implant. Preferably the apo-transferrin is administered by controlled release at or near the implant.

14 Claims, 6 Drawing Sheets

APO-TRANSFERRIN AS A POTENT INHIBITOR OF BACTERIAL ADHESION TO BIOMATERIALS

CROSS-REFERENCE TO RELATED APPLICATIONS

This application claims the benefit of U.S. Provisional Application No. 60/082,177, filed Apr. 16, 1998.

BACKGROUND OF THE INVENTION

This invention relates to a method of inhibiting bacterial adhesion to biomaterials. More particularly, the invention relates to a method of reducing device-associated infections by inhibiting bacterial adhesion to biomaterials with apo-transferrin.

With over 200 million intravascular devices sold annually in the United States, it is apparent that biomedical devices have become an integral part of clinical medicine, and their use is increasing continuously. Infection and thrombosis are often major complications involved with all types of synthetic biomaterials that come in contact with blood, ranging from catheters to artificial hearts. It has been estimated that greater than 45% of hospital infections are related to implants and medical devices. As more devices are implanted and new devices are introduced into clinical use, increasing numbers of patients will be placed at risk for implant-related infection. These complications may be directly attributed to the presence of biomaterial, which is foreign to the human body and provides a suitable substrate for bacterial adhesion at a site sequestered from the body's immunological defenses.

Persistent bacterial infections associated with implant devices remain a serious and costly complication with both temporary and permanent implants. Clinical experience to date suggests that the adherence of bacteria to the biomaterial, resulting in subsequent colonization and biofilm formation, may be the critical event in the pathogenesis of implant-induced infection. Such infections typically are difficult to resolve with antimicrobial therapy, and have been identified as a major cause for patient morbidity, device failure, and explantation.

After blood contacts biomaterial, proteins adsorbed at the interface change the surface characteristics and may provide a suitable substrate for bacteria to adhere and proliferate. Upon bacterial colonization on the surface and formation of biofilm, such a sequestered site may permit pathogenic microorganisms to evade phagocytic cells as well as reduce effective penetration of antibiotics. In many instances, replacement of the infected device is the only successful treatment.

Since the pathogenesis of biomaterial-centered infection is critically dependent on the initial bacterial adhesion to and early growth on a surface, several strategies to disrupt the adhesion process have been suggested. These include incorporating antibiotics or immobilizing antimicrobial peptides into biomaterials and coating biomaterials with surfactants such as salicylic acid, silver, substituted dextran, or polyethylene oxide. The role of serum proteins in mediating bacterial adhesion has been well studied over the past decade. The present inventors, along with other investigators, have shown the antibacterial properties of serum. Recent publications have revealed a strong inhibition of adherence of certain bacteria to biomaterials by whole serum.

In view of the foregoing, it will be appreciated that providing a method for inhibiting bacterial adhesion to biomaterials and reducing infections associated therewith would be a significant advancement in the art.

BRIEF SUMMARY OF THE INVENTION

It is an object of the present invention to provide a method for inhibiting bacterial adhesion to biomaterials used in medical implants.

It is another object of the invention to provide a method for inhibiting implant-associated bacterial infections.

These and other objects can be addressed by providing a method of inhibiting adhesion of bacteria to an implanted device in an individual comprising administering an effective amount of apo-transferrin to the individual. Preferably, the apo-transferrin is administered at or near the implanted device. More preferably, the apo-transferrin is administered by controlled release, such us with microspheres or surface binding and release technologies. In another preferred embodiment of the invention, the apo-transferrin is coupled to a ligand, such as a monoclonal antibody, for targeting the implanted device. Targeting of the ligand-coupled apo-transferrin places the apo-transferrin in close proximity to the device such that its inhibitory effect on bacterial adhesion can be efficacious in reducing implant-associate infection.

Another aspect of the invention comprises a method of reducing device-associated infection in an individual with an implanted device comprising administering an effective amount of apo-transferrin to the individual.

DETAILED DESCRIPTION

Figure 1:
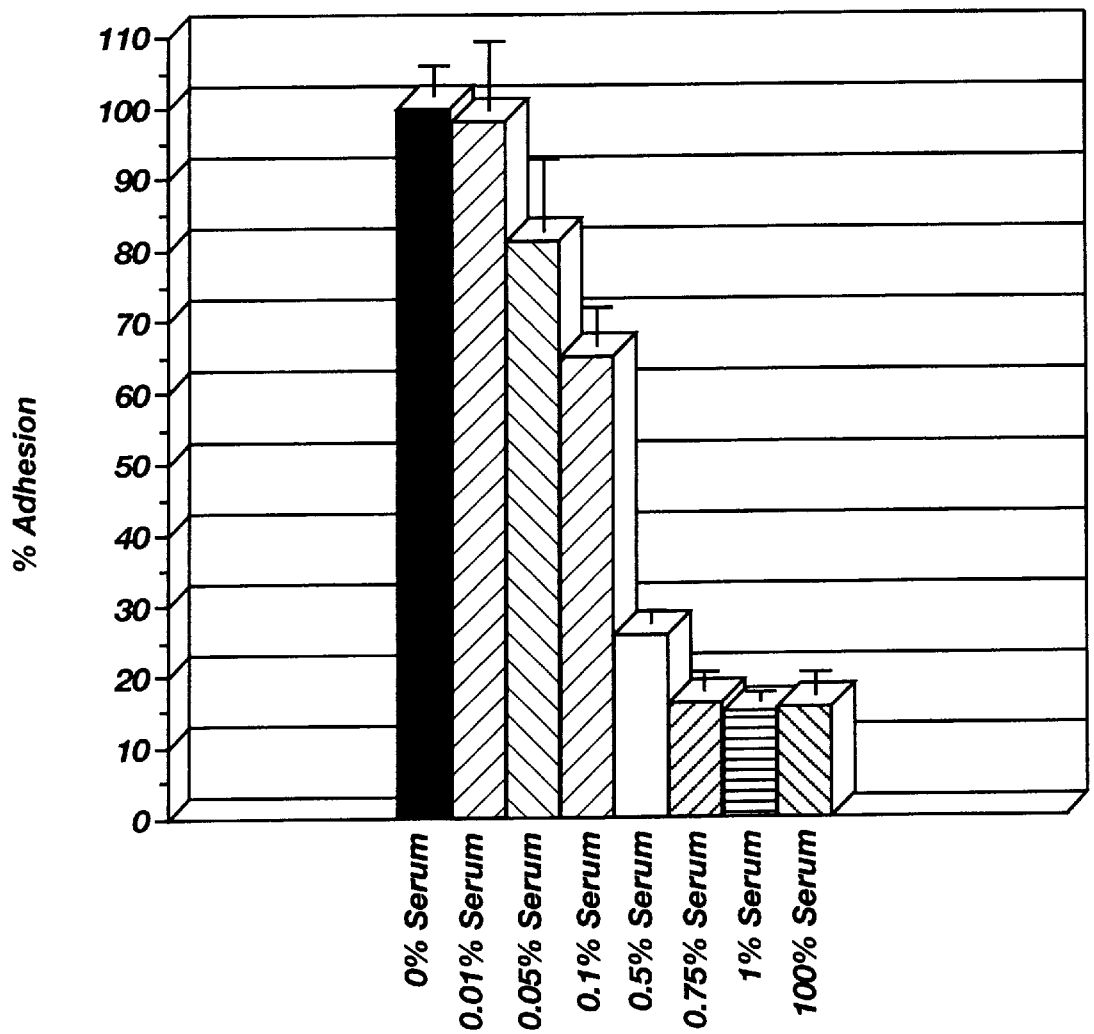
FIG. 1 shows the inhibitory effect of various concentrations of human serum on adhesion of *Staphylococcus epidermidis* to polyurethane (PU) coverslips.

Before the present methods for inhibiting bacterial adhesion to biomaterials and reducing device-associated infections are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. For example, reference to "a device" includes reference to two or more of such devices, reference to "a ligand" refers to one or more of such ligands, and reference to "an antibody" includes reference to two or more of such antibodies.

As used herein, "effective amount" means an amount of apo-transferrin that is nontoxic but sufficient to provide the desired local or systemic effect and performance at a reasonable benefit/risk ratio attending any medical treatment. Preferably, the apo-transferrin is formulated with a pharmaceutically acceptable carrier, according to materials and methods well known in the art.

As used herein, "cfu" or "CFU" means colony forming units, as is well known in the art of microbiology.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "individual" includes humans and warm blooded animals.

As used herein, "administering" and similar terms mean delivering the apo-transferrin to the individual being treated such that the apo-transferrin comes in contact with the implanted device in a pharmaceutically effective amount for inhibiting bacterial adhesion to the device. Thus, the composition is preferably administered to the individual by localized administration, and more preferably is administered by controlled release according to methods well known in the art of drug delivery. Such controlled release can include release from microspheres and surface binding and release. Administration can also include systemic administration, typically by subcutaneous, intramuscular, or intravenous administration, or intraperitoneal administration, wherein the apo-transferrin is conjugated to a ligand that targets and binds the implant. Such ligands include antibodies and, in particular, monoclonal antibodies, which can be prepared according to methods well known in the art. E.g., G. Kohler & C. Milstein, Continuous cultures of fused cells secreting antibody of pre-defined specificity, 256 Nature 495–97 (1975); Wunderlich et al., 17 Eur. J. Cancer Clin. Oncol. 719 (1981); Schlom et al., 77 Proc. Nat'l Acad. Sci. USA 6841 (1980) (human monoclonal antibodies); E. Harlow & D. Lane, Antibodies: A Laboratory Manual (1988) (all of which are hereby incorporated by reference). Coupling of apo-transferrin to the ligand is by methods well known in the art. Injectables for systemic use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

As used herein, "implanted device," "implant," and similar terms refer to medical devices, such as catheters, vascular grafts, artificial organs, and the like that are implanted in the body and come in contact with blood and are therefore susceptible involvement in implantassociated infections and related complications.

Device-associated infection is a serious and costly complication associated with both temporary and permanent implants. Such infections typically are difficult to resolve with antimicrobial therapy, and have been identified as a major cause for patient morbidity, device failure, and explantation. The adherence of bacteria to the biomaterial surface, resulting in subsequent colonization, may be the critical event in the pathogenesis of infection.

An antibacterial activity of a blood component, known as apo-transferrin, is disclosed herein. The anti-bacterial activity of this protein molecule relates to its effective inhibition of bacterial adhesion to surfaces of all biomaterials tested so far. First, it has been noted that the presence of serum in the medium of bacterial culture inhibits bacterial attachment to biomaterial surfaces. Second, the component that exerts such inhibitory activity was isolated upon fractionation of serum, and is herein identified as transferrin. Detailed analysis of this protein-bacterial interaction proves that only apo-transferrin (an iron deficient form of transferrin) exhibits strong inhibition of bacterial adhesion to biomaterial surfaces. The iron-containing form of transferrin, holo-transferrin, does not exhibit this inhibitory effect.

Furthermore, apo-transferrin exhibits similar inhibitory effect on different strains of bacteria, e.g. *Staphylococcus aureus* (Gram positive) and *Pseudomonas aeruginosa* (Gram negative). Surfaces with different protein coatings (collagen, laminin, fibronectin, and poly-D-Lysine) attract a greater number of bacteria compared to unmodified surfaces. However, the presence of apo-transferrin exerts its inhibitory effect regardless of the protein coating. Furthermore, the phenomenon is not due to sequestering free iron and bacterial deprivation of nutritional iron. While the exact mechanism by which apo-Tf inhibits bacterial adhesion is unknown, it is believed that the phenomenon occurs in the fluid phase, and apo-Tf binding onto bacterial surfaces may disrupt the bacterial adhesion mechanism.

When a microorganism invades its host, one of the first steps in the infectious process is the attachment of the microbe to the host tissues. The incidence of infection in patients with implanted devices has been reported to be high, and have proven to pose the greatest long-term threat to device recipient. The pathogenesis of these foreign-body-related infections involves complex interactions that facilitate bacterial adhesion. Thus, the initial bacterial adhesion to and early growth on the surface of an implant could be the most critical events of infection process.

Despite the continuing development of potent antimicrobial agents, biomaterial-centered infections are persistent, thereby limiting the usefulness of many prosthetic devices. It is often reported that these infections cannot be eradicated without surgical revision or implant removal, and infections can result in morbidity, amputation, or death.

Recognizing the significant event of bacterial adhesion to biomaterials in the process of infection, efforts have been directed towards disrupting this crucial step. Many investigators have described the possibility of incorporating antimicrobial or antiadhesive agents into the indwelling devices. Such surface bound molecules may reduce the adhesion of bacteria by presenting an unattractive surface for the invading microbes. Furthermore, others have alluded to the possibility of the release of antibacterial peptides in the vicinity of an implant. The results presented herein indicate that apo-Tf is the active component of serum with the ability to diminish bacterial adhesion to biomaterials. Furthermore, two lines of direct evidence from this investigation support this finding. First, purified apo-Tf obtained commercially, added to the medium was demonstrated to inhibit bacterial adhesion. Second, the removal of Tf from serum by affinity chromatography abolished the inhibitory effect of serum.

EXAMPLE 1
Effect of Serum on Bacterial Adhesion

In this example, adhesion studies were conducted to examine the ability of bacteria to adhere to various substrates in the presence of serum in the medium. Whole human serum was examined for its effect on bacterial adhesion to polyurethane (PU) Tecoflex® coverslips. Briefly, PU coverslips were cleaned with 70% propanol and were then sterilized by ethylene oxide and aerated for 16 hrs. Next, the sterile coverslips were incubated with selected concentrations of serum in Hanks Balanced Salt Solution (HBSS; Sigma Chemical Co., St. Louis, Mo.), and 100 $\mu$l of $5\times10^7$ CFU/ml of $^{111}$In-oxine labeled bacteria was added to the medium.

Cultures of *Staphylococcus epidermidis* (ATCC No. 12228) were obtained from Richard's Laboratory Inc. (Pleasantville, Utah.). Suspensions containing $1\times10^6$ CFU/ml were stored in a medium comprising 10% of sterilized biologic grade glycerin (Sigma) and tryptic soy broth (TSB) (Remel Co., Lenexa, Kans.) in 1-ml sterile glass vials at $-70°$ C. Samples were thawed, added to 20 ml of TSB, and cultured for 24 hrs at 37° C. The cell suspension was centrifuged at 1200 g for 15 minutes at 4° C. and washed with phosphate-buffered saline (0.014 M $Na_2HPO_4$, 0.003 M $NaH_2PO_4$, 0.15 NaCl, pH 7.4, PBS). Cultures of bacteria at $5\times10^7$ CFU/ml were labeled with 100 $\mu$Ci of $^{111}$Indium-oxine as described in R. Ardehali & S. F. Mohammad, $^{111}$Indium Labeling of Microorganisms to Facilitate the Investigation of Bacterial Adhesion, 27 J. Biomed. Mater. Res. 269–275 (1993) (hereby incorporated by reference). After 2 hrs of incubation with the radiolabel agent, bacteria were washed three times in PBS, and resuspended in HBSS.

The test chamber was incubated at 37° C. and 90% RH on a rotator for 2 hrs. At the end of incubation, surfaces were rinsed 3 times with 3 ml of PBS to remove non-adherent bacteria. Bacterial adhesion to a test surface was then quantitated by gamma counting in a Packard 5000 gamma counter. Representative samples were fixed in Karnovsky's fixative, dehydrated in graded alcohol, critical-point-dried, coated with gold-palladium, and examined under a JEOL SM-35 Scanning Electron Microscope (SEM).

FIG. 1 shows the inhibitory effect of human serum on adhesion of *S. epidermidis* to PU coverslips. The presence of at least about 0.75% serum in the medium resulted in about 85% inhibition of adhesion.

EXAMPLE 2

Figure 2:
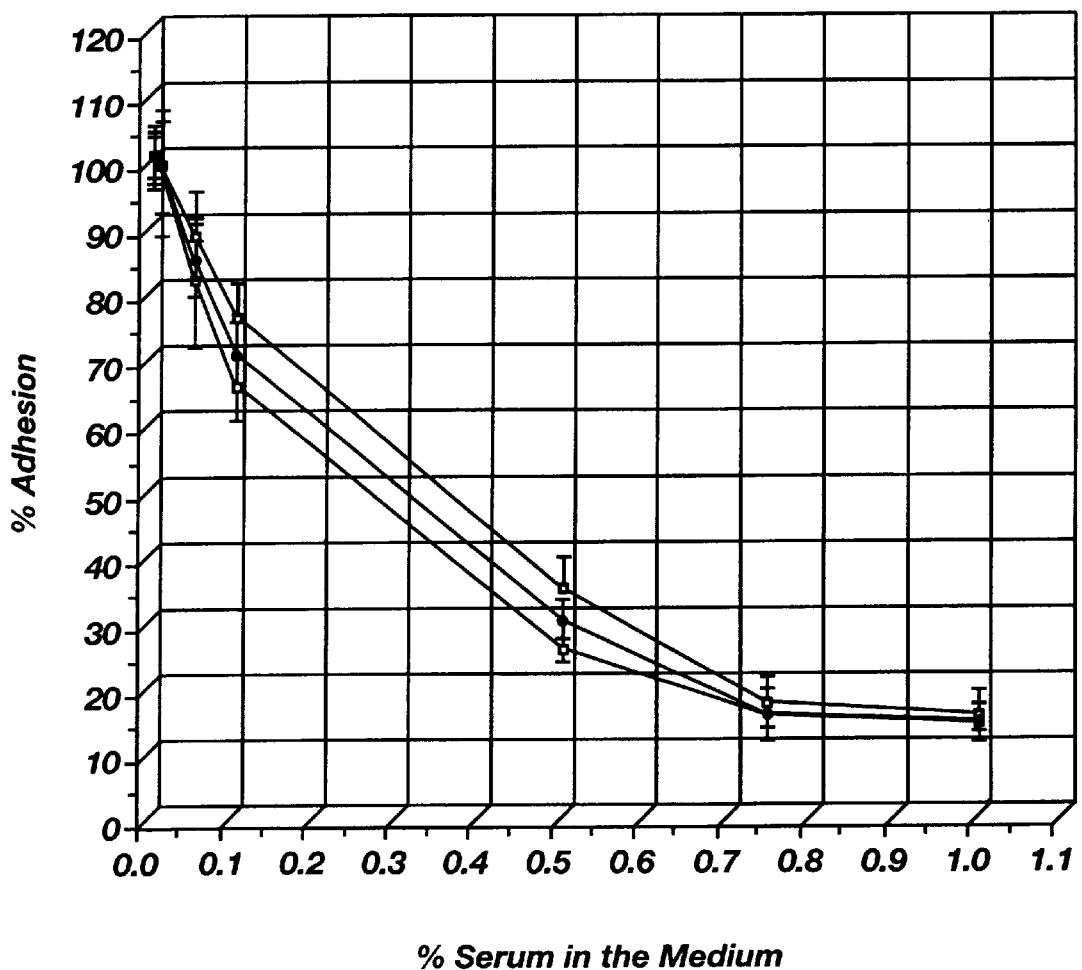
FIG. 2 shows the effects on adhesion of *S. epidermidis* to polyurethane coverslips in the presence of serum (□), plasma poor platelets (♦), and plasma rich platelets (■).

To determine whether the inhibition of adhesion shown in Example 1 was unique to serum, plasma poor platelets (PPP) and plasma rich platelets (PRP) were prepared from the same donor pool according to the procedure described in I. W. Wang et al., Adhesion to Hydrophobic Biomedical Polymer Is Mediated by Platelets, 167 J. Infect. Dis. 329–336 (1993) (hereby incorporated by reference). Furthermore, various surfaces, including polyurethane, glass, and polystyrene, were tested for bacterial adhesion in the presence of serum, PPP, or PRP. Polyurethane coverslips were cleaned as described in Example 1. Glass coverslips were cleaned in a 40° C. chromage (Monostat, N.Y.) solution for 45 minutes and washed in filtered, reverse osmosis water for 15 minutes. The coverslips were then sterilized with ethylene oxide and aerated for 16 hours. For polystyrene surfaces, multiwell culture dishes (Falcon) were used. The polyurethane and glass coverslips and polystyrene culture dishes were then incubated with radioactively labeled bacteria according to the procedure of Example 1. A five-fold decline in *S. epidermidis* adhesion to PU was noted in the presence of serum diluted as low as 0.5% by volume in HBSS at the end of two hrs incubation. PPP and PRP exhibited similar inhibitory effects under similar controlled conditions (FIG. 2).

EXAMPLE 3

In this example, the procedure of Example 2 was followed except that *Staphylococcus aureus* (ATCC No. 25923) and *Pseudomonas aeruginosa* (ATCC No. 27852), obtained from Richard's Laboratories Inc., were tested. The results were substantially identical to those described in Examples 1 and 2.

EXAMPLE 4

Figure 3:
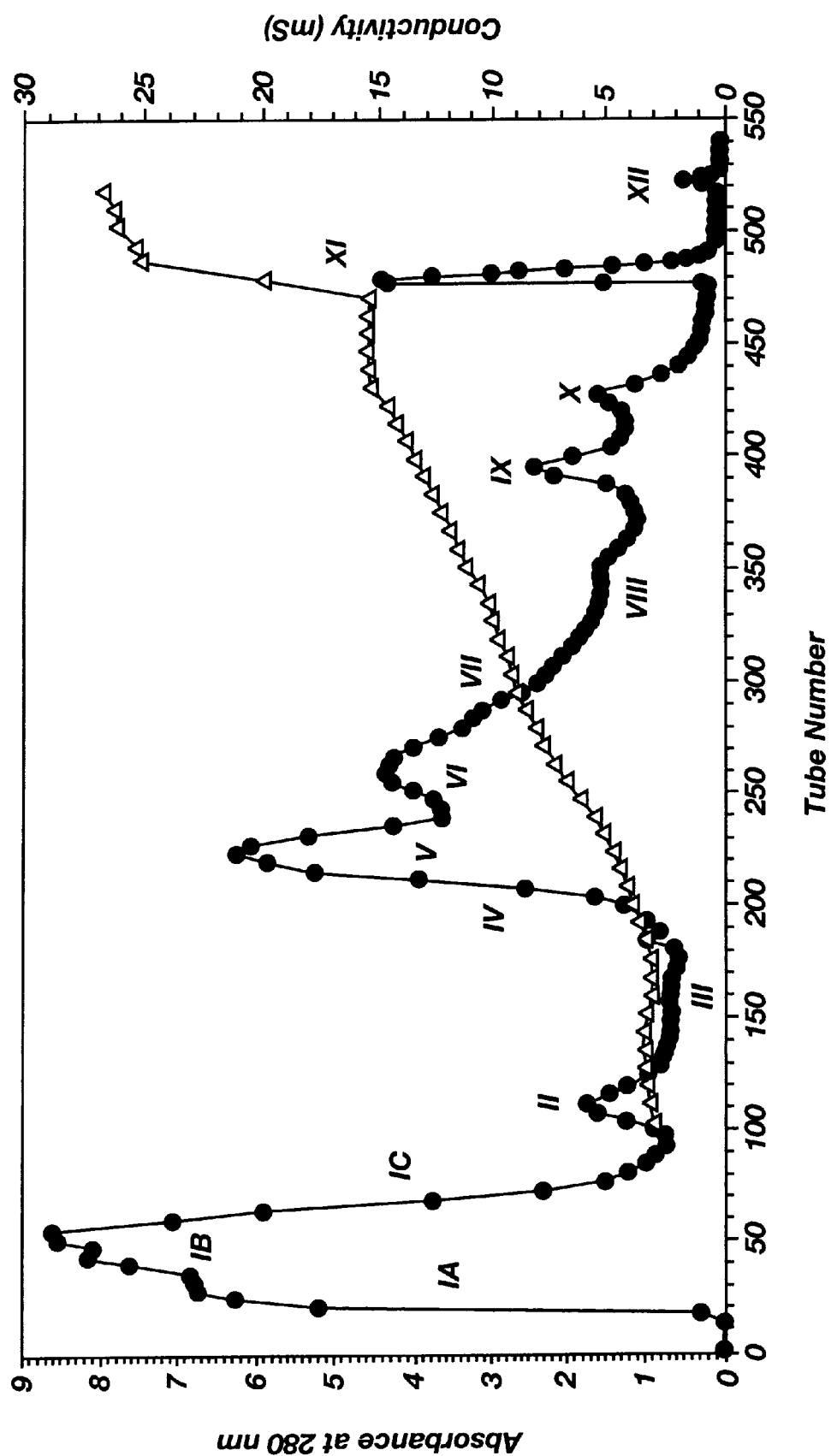
FIG. 3 shows fractionation of bovine serum by anion exchange chromatography on Q-Sepharose®, with absorbance at 280 nm (●) and conductivity (mS; Δ) shown as a function of—tube number; a total of 14 protein fractions were collected (IA–C, II–XII).

Bovine serum was fractionated by column chromatography on a strong anion exchanger, Q-Sepharose®. In brief, the serum sample was adjusted to the conductivity of buffer A (20 mM sodium phosphate, pH of 7.4, 20 mM NaCl), and applied to a Q-Sepharose® column (5.0 cm i.d., gel bed 23 cm high) pre-equilibrated with buffer A. A total of 14 protein pools were collected based on elution protein profile and patterns obtained by SDS-PAGE (described below). The majority of immunoglobulins (fractions IA, IB, IC, II, and III) were eluted with an initial wash of buffer A (2 liters). Further proteins (fractions IV through IX) were eluted with a linear salt gradient containing 20 mM sodium phosphate, pH of 7.4, and from 20 to 220 mM NaCl (2.5 liters each). At the end of a gradient, elution of fraction X was completed with 20 mM sodium phosphate, pH of 7.4, 220 mM NaCl. An application of 20 mM sodium phosphate, pH of 7.4, 400 mM NaCl resulted in the elution of proteins in the fractions XI and XII. Flow rate was maintained between 100–130 mL/hr, depending on the stage of fractionation. Approximately 18 ml (360 drops) of eluent per tube were collected. FIG. 3 shows the elution profile that was derived from the absorbance values measured at 280 nm on aliquots of fractions diluted 1:10. These were used for calculation of protein concentrations using an average absorption coefficient of 10.

Figure 4A:
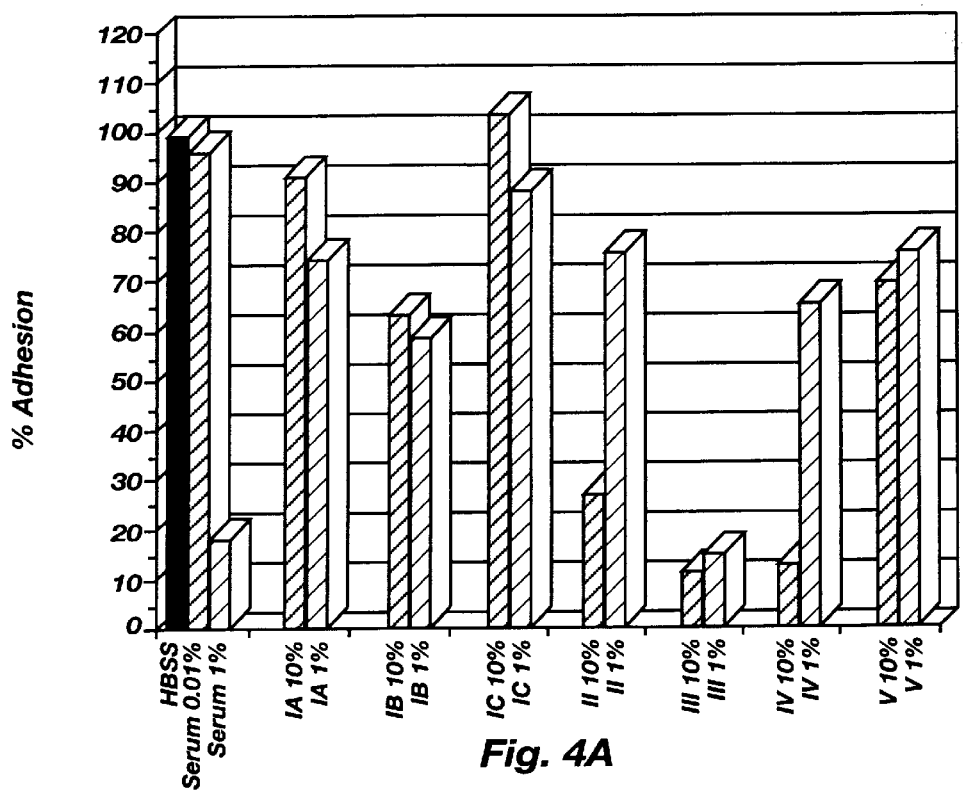
FIGS. 4A–B show adhesion of *S. epidermidis* to polyurethane in the presence of serum protein fractions of FIG. 3; HBSS and dilute serum were used as controls.
Figure 4B:
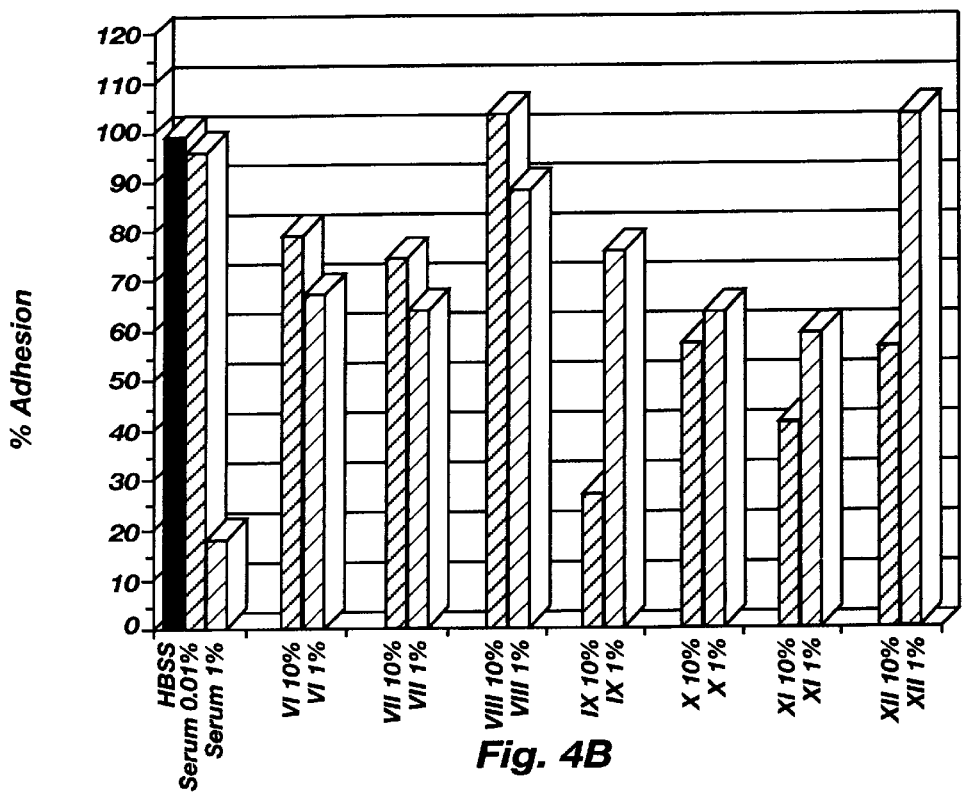

All protein fractions were examined for their effect on *S. epidermidis* adhesion to PU at 10% and 1% by volume dilution, according to the procedure of Example 1. Fractions III and IV were identified as the fractions containing the most potent inhibitory serum components (FIGS. 4A–B). Scanning electron microscopy supported these findings.

All fractions were analyzed by polyacrylamide gel electrophoresis (PAGE) in the presence of sodium dodecyl sulfate (SDS) under non-reducing and reducing conditions. To shed more light as to the identity of proteins in the individual fractions, all fractions were subjected to immunoelectrophoretic analysis. Fraction III, which exhibited a significant inhibitory effect, was further analyzed by protein sequencing, e.g., W. Dubiel et al., 267 J. Biol. Chem. 22699 (1992); P. Edman & G. Begg, 1 Eur. J. Biochem. 80 (1967) (hereby incorporated by reference), and western blot analysis, H. Towbin et al., 76 Proc. Nat'l Acad. Sci. USA 4350 (1979); W. N. Burnette, 112 Anal. Biochem. 192–203 (1981) (hereby incorporated by reference), with enhanced chemiluminescence detection (WB-ECL) to identify the inhibitory component in this fraction.

Figure 5C:
FIGS. 5A–C show identification of transferrin as the major protein component of fractions III and IV. SDS-PAGE analyses of fractions III and IV, along with apo-transferrin ($Tf_a$) and holo-transferrin ($Tf_h$), under nonreducing (FIG. 5A) and reducing conditions (FIG. 5C), revealed that two major bands in these two fractions correspond to transferrin (Tf). The bands associated with immunoglobulins (Ig), heavy chains (H), and light chains (L) are also indicated. Western blot analysis with enhanced chemiluminescence detection (WB-ECL) further confirmed these results, as rabbit anti-human Tf antibody reacted with two major bands in fractions III and IV, and those of both apo- and holo-transferrin (FIG. 5B).
Figure 5B:
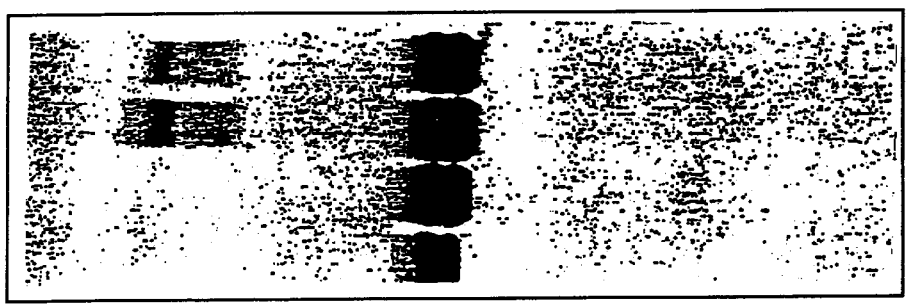
Figure 5A:
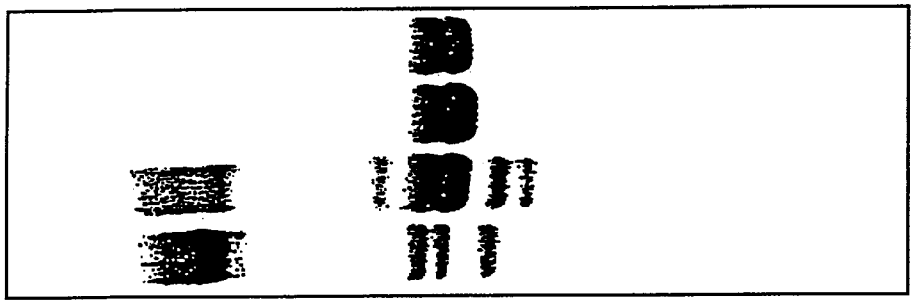

Amino acid sequencing along with immunoelectrophoretic analysis revealed the presence of transferrin as the major component in this fraction, along with small quantities of IgG and plasminogen. Furthermore, SDS-PAGE analyses of fractions III and IV, along with purified commercial apo-transferrin and holotransferrin, under non-reducing and reducing conditions indicated that the two major bands in these two fractions correspond to transferrin. Western blot analysis with enhanced chemiluminescence detection (WB-ECL) further confirmed these results, as rabbit anti-human Tf antibody reacted with two major bands in fractions III and IV, and those of both apo- and holo-Tf (FIGS. 5A–C).

EXAMPLE 5
Inhibition of Bacterial Adhesion by Apo-Tf

Once it was demonstrated that transferrin is the major component in the active fraction, bacterial adhesion assays were performed with purified transferrin obtained commercially. Human and bovine transferrin in both holo- and apo-form were purchased from Sigma (St. Louis, Mo.). Adhesion assays were performed, according to the procedure of Example 1, using Tf in its soluble form in the medium.

Figure 6:
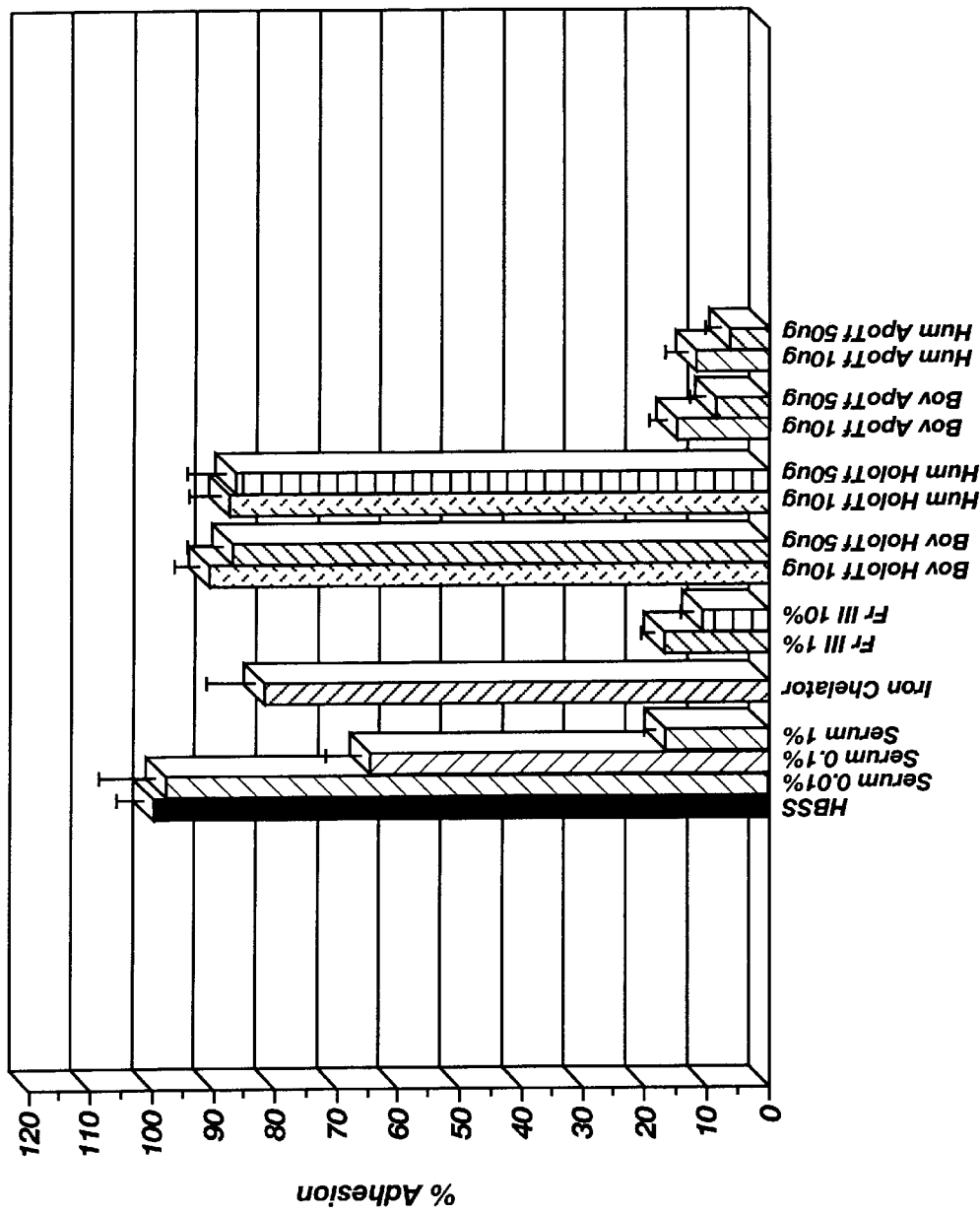
FIG. 6 shows the effect of HBSS, serum, an iron chelator (0.2 μM 2,2'-dipyridyl), bovine serum fraction III (FR III), bovine holo-transferrin (Bov Holo Tf), human holo-transferrin (Hum Holo Tf), bovine apo-transferrin (Bov Apo Tf), and human apo-transferrin (Hum Apo Tf), on bacterial adhesion to a polyurethane surface.

Experimental results showed that the inhibitory effect was exerted by apo-Tf but not holo-Tf (FIG. 6). A greater than four-fold decrease in S. epidermidis adhesion to PU was noticed when apo-Tf was present at as low a concentration as 10 $\mu$g/ml compared to the same concentration of holo-Tf. The inhibition of bacterial adhesion was shown not to be due to iron deprivation, as 0.2 $\mu$M 2,2'-dipyridyl, a synthetic iron chelator, did not cause such inhibitory effect. Bovine and human apo-transferrin yielded substantially identical results.

EXAMPLE 6

In the this example, the procedure of Example 5 was followed except that S. aureus and P. aeruginosa were substituted for S. epidermidis. The results were substantially identical, showing that apo-transferrin inhibits adhesion of both Gram-positive and Gram-negative bacteria.

EXAMPLE 7
Effect of Apo-Tf on Bacterial Adhesion to Protein Coated Surfaces

Biocoat Matrigel plates (Collaborative Biomedical Products, Bedford, Mass.) covered with collagen type IV, laminin, fibronectin, or poly-D-lysine were tested for bacterial adhesion in the presence or absence of apo-Tf according to the procedure of Example 1. Following incubation with non-radiolabeled bacteria, surfaces were washed and fixed. They were viewed using a light microscope, and 8 random fields were selected and the number of adhered bacteria was counted.

Bacterial adhesion significantly increased on surfaces covered with collagen, laminin, fibronectin, or poly-D-lysine, compared to unmodified surfaces. The presence of apo-Tf at 50 $\mu$g/ml in the medium, however, inhibited adhesion regardless of the protein coating.

EXAMPLE 8
Role of Apo-Tf on the Surface and in the Medium

To determine whether apo-Tf inhibits bacterial adhesion by coating the surface, thus rendering bacteria from adhering, polystyrene surfaces were coated with 20 $\mu$g/ml of apo-Tf according to the adsorption isotherm. Amounts of apo-Tf bound to the surface were determined by quantitative ELISA inhibition assay. Experimental results revealed no difference between apo-Tf coated vs. uncoated surfaces. However, the introduction of apo-Tf in soluble form into the medium reinforced the inhibition of bacterial adhesion, suggesting the activity of apo-Tf to be in the fluid phase. Treatment of S. aureus with apo-Tf for 2 hrs inhibited the ability of bacteria to attach to a variety of uncoated or coated surfaces.

EXAMPLE 9

In this example, apo-transferrin was removed from serum by affinity chromatography using anti-transferrin antibodies. The resulting apo-transferring-depleted serum was then tested for the ability to inhibit adhesion of S. epidermidis according to the procedure of Example 1. The results of this experiment showed that depletion of apo-transferrin from the serum abolished the ability of the serum to inhibit bacterial adherence to surfaces.

References

1. R. Ardehali and S. F. Mohammad: [111]Indium Labeling of Microorganisms to Facilitate the Investigation of Bacterial Adhesion. J Biomed Mater Res 27:269–75 (1993).
2. D. E. Benson, G. L. Burns, and S. F. Mohammad: Effects of Plasma on Adhesion of Biofilm Forming Pseudomonas aeruginosa and Staphylococcus epidermidis to Fibrin Substrate. ASAIO J 42:M655-M660 (1996).
3. S. F. Mohammad: Association Between Thrombosis and Infection. ASAIO J 40 226–30 (1994).
4. Y. H. An, G. W. Stuart, S. J. McDowell, S. E. McDaniel, Q. Kang, and R. J. Friedman: Prevention of Bacterial Adherence to Implant Surfaces with a Crosslinked Albumin Coating In Vitro. J Orthop Res 14:846–49 (1996).
5. P. Williams and E. Griffiths: Bacterial Transferrin Receptors-Structure, Function and Contribution to Virulence. Med Microbiol Immunol 181:301–322 (1992).
6. R. T. Ellison, T. J. Giehl, and F. M. LaForce: Damage of the Outer Membrane of Enteric Gram-Negative Bacteria by Lactoferrin and Transferrin. Infect Immun 56:2774–81 (1988).
7. R. T. Ellison, F. M. LaForce, T. J. Gichl, D. S. Boose, and B. E. Dunn: Lactoferrin and Transferrin damage of the Gram-Negative Outer Membrane is Modulated by $Ca^{2+}$ and $Mg^{2+}$. J Gen Microbiol 136:1437–46 (1990).
8. R. T. Ellison: The Effect of Lactoferrin on Gram-Negative Bacteria: Lactoferrin :Structure and Function 71–90 (1994).
9. R. R. Arnold, M. F. Cole, and J. R. McGhee: A Bactericidal Effect for Human Lactoferrin. Nature 197:263–65 (1977).
10. J. Stuart, S. Norrell, and J. P. Harrington: Kinetic Effect of Human Lactoferrin on the Growth of Escherichia Coli 0111. Int J Biochem 16:1043–47(1984).

11. J. Erdei, A. Forsgren, and S. Naidu: Lactoferrin Binds to Porins OmpF and OmpC in *Escherichia Coli*. Infect Immun 62:1236–40 (1994).
12. W. Bellamy, M. Takase, K. Yamauchi, H. Wakabayashi, K. Kawase, and M. Tomita: Identification of the Bactericidal Domain of Lactoferrin. Biochem biophys Acta 1121:130–136(1992).
13. E. Elass-Rochard, A. Roseanu, D. Legrand, M. Trif V. Salrnon, C. Motas, J. Montreuil, and G. Spik: Lactoferrin-Lipopolysaccharide Interaction: Involvement of the 28–34 Loop region of Human Lactoferrin in the High-Affinity binding to *Escherichia Coli* 055B5 Lipopolysaccharide. Biochem J 312:839–45 (1995).
14. C. Dalmastri, P. Valenti, P. Visca, P. Vinorioso, and N. Orsi: Enhanced Antimicrobial Activity of Lactoferrin by Binding to the Bacterial Surface. Microbiological 11:225–30 (1988). P. Francois, P. Vaudaux, T. J. Foster, and D. P. Lew: Host-Bacteria Interactions in Foreign Body Infections. Infect Control Hosp Epidemiol 17:514–20 (1996).
15. W. M. Artis, E. Patrusky, F. Rastinejad, and R. Duncan: Fungastic Mechanism of Human Transferrin for Rhizopus oryzae and Trichophton mentagrophytes: Alternative to Simple Iron Deprivation. Infect Immun 41:1269–1278 (1983).
16. B. van Haeringen, F. de Lange, I. H. M. van Stokkam, S. K. S. Srai, R. W. Evans, R. van Grondelle, and M. Bloemendal: Dynamic Structure of Human Serum Transferrin From Transient Electric Birefringence Experiments. Proteins: Structure, and Genetics 23:233–40 (1995).
17. P. E. Vaudaux, P. Francois, R. A. Proctor, D. McDevitt, T. J. Foster, R. M. Albrecht, D. P. Lew, H. Waber, and S. L. Cooper: Use of Adhesion-Defective Mutant of Staphylococcus aureus to Define the Role of Specific Plasma Proteins in Promoting Bacterial Adhesion to Canine Arteriovenous Shunts. Infect Immun 63:585–90 (1995).
18. M. van der Flier, N. Chhun, T. M. Wizemann, J. Min, J. B. McCarthy, and E. I. Toumanen: Adherence of Streptococcus pneumonia to Immobilized Fibronectin. Infect Immun 63:4317–22 (1995).
19. I. W. Wang, J. M. Anderson, R. E. Marchant: Staphylococcus epidermidis Adhesion to Hydrophobic Biomedical Polymer is Mediated by Platelets. J Infect Dis 167:329–36 (1993).

We claim:

1. A method of inhibiting adhesion of bacteria to an implanted device in an individual comprising administering to said individual an amount of apo-transferrin effective for inhibiting bacterial adhesion to the device.
2. The method of claim 1 wherein said apo-transferrin is administered at or near the implanted device.
3. The method of claim 2 wherein said apo-transferrin is administered by controlled release.
4. The method of claim 3 wherein said apo-transferrin is administered in microspheres.
5. The method of claim 3 wherein said apo-transferrin is administered by surface binding and release.
6. The method of claim 1 wherein said apo-transferrin is coupled to a ligand for targeting the implanted device.
7. The method of claim 6 wherein said ligand is a monoclonal antibody.
8. A method of reducing device-associated infection in an individual with an implanted device comprising administering an effective amount of apo-transferrin to said individual.
9. The method of claim 8 wherein said apo-transferrin is administered at or near the implanted device.
10. The method of claim 9 wherein said apo-transferrin is administered by controlled release.
11. The method of claim 10 wherein said apo-transferrin is administered in microspheres.
12. The method of claim 10 wherein said apo-transferrin is administered by surface binding and release.
13. The method of claim 8 wherein said apo-transferrin is coupled to a ligand for targeting the implanted device.
14. The method of claim 13 wherein said ligand is a monoclonal antibody.

* * * * *